United States Patent [19]

Caporiccio

[11] Patent Number: 5,493,049
[45] Date of Patent: Feb. 20, 1996

[54] FLUORINATED COMPOUNDS CONTAINING HETERO ATOMS AND POLYMERS THEREOF

[75] Inventor: Gerardo Caporiccio, Midland, Mich.

[73] Assignee: Dow Corning Corporation, Midland, Mich.

[21] Appl. No.: 247,824

[22] Filed: May 20, 1994

Related U.S. Application Data

[62] Division of Ser. No. 15,737, Feb. 10, 1993, Pat. No. 5,350,878.

[51] Int. Cl.$^6$ ........................................ C07C 69/63
[52] U.S. Cl. ........................ 560/227; 560/180; 560/197; 560/229; 560/144
[58] Field of Search ........................... 560/227, 180, 560/144, 197, 229

[56] References Cited

U.S. PATENT DOCUMENTS

| | | | |
|---|---|---|---|
| 2,817,678 | 12/1957 | Barnhart | 260/487 |
| 3,452,074 | 6/1969 | Weesner | 260/463 |
| 3,632,641 | 1/1972 | Fielding | 260/539 |
| 3,790,607 | 2/1974 | Lichstein | 260/408 |
| 4,072,726 | 2/1978 | Nychka et al. | 260/633 |
| 4,478,760 | 10/1984 | Blancou et al. | 260/465.7 |
| 4,578,503 | 3/1986 | Ishikawa et al. | 560/82 |
| 4,855,487 | 8/1989 | Fuchikami et al. | 560/227 |

FOREIGN PATENT DOCUMENTS

| | | | |
|---|---|---|---|
| 62-45562 | 2/1987 | Japan | C07C 69/63 |
| 63-45237 | 2/1988 | Japan | C07C 69/63 |

*Primary Examiner*—Paul J. Killos
*Attorney, Agent, or Firm*—Robert Spector

[57] ABSTRACT

This invention provides 1) novel reactive fluorinated compounds derived from a specified class of telomers or cotelomers of fluoroolefins; and 2) stable products and stable polymers thereof obtained by reaction or polycondensation of the novel reactive fluorinated compounds with specified classes of hydrogenated aliphatic, alicyclic, aromatic reactive compounds, telechelic oligomers and block polymers wherein said stable products and polymers contain hetero atoms such as oxygen, sulfur or nitrogen and are characterized by high thermal and chemical resistance.

2 Claims, No Drawings

FLUORINATED COMPOUNDS CONTAINING HETERO ATOMS AND POLYMERS THEREOF

This is a divisional of copending application(s) Ser. No. 08/015,737 filed on Feb. 10, 1993, now U.S. Pat. No. 5,350,878.

BACKGROUND OF THE INVENTION

1. Field of the Invention

This invention relates to novel classes of fluorinated compounds that according to their structure and molecular weight can be chemically reactive or chemically inert. This invention also relates to polymers characterized by high thermal and chemical resistance.

2. Reference to Related Applications

This application is a continuation-in part of application Ser. No. 07/718,663, filed on Jun. 21, 1991, which is, in turn, a continuation-in-part of application Ser. No. 07/385,119, filed on Jul. 26, 1989.

BACKGROUND INFORMATION

U.S. Pat. No. 2,817,678, which issued to Barnhart on Dec. 24, 1957 describes fluorine-containing polymers and telomers prepared by the peroxide-initiated telomerization of fluorinated olefins in the presence of an alkyl halocarbonate as the telogen. The final telomers and cotelomers contain the terminal group —C(O)OR, where R represents the alkyl radical present on the initial halocarbonate.

SUMMARY OF THE INVENTION

One objective of the present invention to provide stable derivatives of certain fluorocarbon telomers that are useful as high performance lubricants, hydraulic fluids, anti-wear additives for high performance lubricants, electrically insulating fluids, or thermoplastic elastomers, or resins that can be selectively used as sealants, high consistency rubbers, coatings, engineering polymers or as additives for high performance polymers. The polymers find application in advanced technologies such as aerospace, electronics, communications and high temperature engines.

Another objective of the invention is to modify existing polymers or existing telechetic polymer blocks by linking to them selected fluorinated telomers in order to impart specific desired properties. The properties common to all of the final products of this invention include thermochemical resistance, low friction and wear characteristics, good rheological properties (for elastomer and liquids) good mechanical properties, workability for highly consistency polymers, and good electrical properties.

The objectives of this invention are achieved by providing stable products, including polymers, derived from the reaction of 1) reactive fluorinated compounds derived from a specified class of telomers or cotelomers of fluoroolefins, and 2) specified classes of hydrogenated aliphatic, alicyclic and aromatic reactive compounds, telechelic oligomers and block copolymers. The stable products and polymers contain hetero atoms such as oxygen, sulfur or nitrogen and are characterized by high thermal and chemical resistance.

DETAILED DESCRIPTION OF THE INVENTION

The fluorinated compounds of this invention are represented by a formula selected from the group consisting of $$R^1R^2_zX, \quad \text{I}$$

$$R^3(R^2_zR^1)_j \quad \text{II}$$

and $$R^1[(R^2_zR^4)_v(R^2_zR^5_y)_w]_kR^2_zR^1, \quad \text{III}$$

where X represents a reactive group selected from the group consisting of chlorine, bromine, iodine, hydroxyl, toluensulfonyloxy, amino, cyano, isocyanato, mercapto and carboxy, and X is bonded to a carbon atom of $R^2$ $R^1$ is selected from the group consisting of (a) monovalent telomers of a fluorinated olefin selected from the group consisting of chlorotrifluoroethylene, vinylidene fluoride and trifluoroethylene, and (b) monovalent cotelomers of combination of fluorinated olefins selected from the group consisting of (1) chlorotrifluoroethylene and a fluoropropene selected from the group consisting of hexafluoropropene and 2-hydropentafluoropropene, (2) chlorotrifluoroethylene and hexafluoropropene, (3) chlorotrifluoroethylene and tetrafluoroethylene, (4) chlorotrifluoroethylene, tetrafluoroethylene and a fluoropropene selected form the group consisting of hexafluoropropene and 2-hydropentafluoropropene, (5) vinylidene fluoride and a fluoropropene selected from the group consisting of hexafluoropropene, 1-hydropentafluoropene and 2-hydropentafluoropropene (6) tetrafluoroethylene and a perfluoroalkyl vinyl ether, (7) tetrafluoroethylene, chlorotrifluoroethylene and a perfluoroalkyl vinyl ether, (8) tetrafluoroethylene and a perfluoroalkyl vinyl ether, and (9) tetrafluoroethylene, vinylidene fluoride and a fluoropropene selected from the group consisting of hexafluoropropene, 1-hydropentafluoropropene and 2-hydropentafluoropropene, where the alkyl radicals of said perfluoroalkyl vinyl ethers contain from 1 to 3 carbon atoms;

$R^2$ represents a bivalent radical connecting $R^1$ with X, $R^3$, $R^4$, or $R^5$ and is selected from the group consisting of dimethylene, trimethylene, ethyleneoxy, trimethyleneoxy, trimethyleneoxy, tetramethyleneoxy, 2-hexafluoro-2 propyleneoxy, 2,2-dimethyl-1,3-propylenedioxy, hexafluoroisopropylidene and 2,2-dimethyl-1,3-trimethylene;

$R^3$ represents a polyvalent radical selected from the group consisting of 2,2-dimethyleneoxypropane, 1,1,1-tris(methyleneoxy)ethane, 1,1,1-tris(methyleneoxy)propane, tetra(methyleneoxy)methane, 1,3-phenylene, 1,4-phenylene, oxy, thio, dithio, phenylenedithio, 1,1,1,5,5,5-hexa(methyleneoxy)-3-oxapentane and $R^4$;

$R^4$ represents a bivalent radical derived from telomers or cotelomers obtained from the same group of olafins and perfluoroalkyl vinyl ethers as R1, $R^5$ represents a telechelic oligomer derived from a compound selected from the group consisting of aromatic carbonates, aromatic ether-ketones, aromatic ether sulfones, aromatic imides, aromatic ether-imides, aromatic amides, aliphatic amides, cycloaliphatic amides, aromatic ethers and aromatic thioethers, aromatic esters, aliphatic esters, heterocyclic aromatic amidourethanes, aliphatic urethanes and aromatic urethanes; j is from 2 to 6, inclusive; z is 1 or 2; v is from 1 to 10, inclusive; w is from 1 to 10, inclusive; y is from 1 to 100, inclusive; and k is from 1 to 500, inclusive.

Preferred embodiments of $R^1$ correspond to the formulae:
$R_f(C_2ClF_3)_n$—$CF_2CF(R^6)$—$C_1H_{21}$—, $R_f(C_2ClF_3)_p$—$(C_3F_6)_q$—$C_3F_6$—$C_1H_{21}$—, $R_f(C_2F_4)_t(C_2ClF_3)_u$—$(C_3F_6)$ $_q$—CF$_2$CF(R$^6$)—C$_l$H$_{2l}$—, R$_f$(C$_2$F$_4$)$_t$(C$_2$ClF$_3$) $_u$—[C$_2$F$_3$ (ORf)]$_q$C$_2$F$_4$—C$_l$H$_{2l}$—, R$_f$(C$_2$H$_2$F$_2$)$_p$(C$_3$F$_6$)$_q$—C$_l$H$_{2l}$—, R$_f$(C$_2$F$_4$)$_p$—[C$_2$F$_3$(ORf)]$_q$—C$_l$H$_{2l}$—, R$_f$(C$_2$H$_2$F$_2$)$_t$(C$_2$F$_4$)$_u$(C$_3$F$_6$)$_q$—C$_l$H$_{2l}$— and R$_f$(C$_2$ClF$_3$)$_p$[C$_2$F$_3$(OR$_f$)]$_q$—CF$_2$CF(R$^6$)—C$_l$H$_{2l}$—.

In these formulae R$_f$ is —CF$_3$, —C$_2$F$_5$, —C$_3$F$_7$, or —C$_4$F$_9$;

R$^6$ represents fluorine or a trifluoromethyl group;

the value of l is 2, 3 or 4; the value of n is from 1 to 20, inclusive, preferably from 1 to 10;

the value of p/q is from 2 to 10, inclusive and the value of p+q is from 2 to 20, preferably from 2 to 10;

the value of t+u/q is from 2 to 10, inclusive, the value of t/u is from 0.1 to 10, and the value of t+u+q is from 2 to 20, inclusive, preferably lower than 10; and the value of n is from 1 to 20, inclusive, preferably from 1 to 10.

The repeating units of the copolymers are randomly distributed along the chain.

The divalent radical R$^2$ that connect R$^1$ with X, R$^3$, R$^4$, or R$^5$. R$^2$ radicals of identical or different structure can be connected to different atoms of polyvalent radicals. Sequences of two R$^2$ radicals are permitted, with the proviso that the two R$^2$ radicals are not identical. For example, the sequence —CH$_2$CH$_2$OCH$_2$CH$_2$— is permitted, but —CH$_2$CH$_2$OCH$_2$CH$_2$O— is not.

R$^2$ is selected from the group consisting of:

| | |
|---|---|
| —CH$_2$CH$_2$— | dimethylene |
| —CH$_2$CH$_2$CH$_2$— | trimethylene |
| —CH$_2$CH$_2$O— | ethylenoxy |
| —CH$_2$CH$_2$CH$_2$O— | trimethyleneoxy |
| —COCH$_2$— | oxoethylene |
| —COCH$_2$— | oxoethylene |
| —COCH$_2$CH$_2$— | oxotrimethylene |
| —COCH$_2$CH$_2$CH$_2$— | oxotetramethylene |
| —C(CF$_3$)$_2$—O— | bis(trifluoromethyl)methyleneoxy |
| —(CH$_3$)$_2$C(CH$_2$O—)$_2$— | 2,2-dimethyl-1,3-propylenedioxy |
| —C(CF$_3$)$_2$— | hexafluoro isopropylidene, and |
| —(CH$_3$)$_2$C(CH$_2$—)$_2$— | 2,2-dimethyl-1,3-trimethylene |

If more than one R$^2$ radical is present in a compound, these can be identical or different.

R$^3$ is a radical selected from:

| | |
|---|---|
| (CH$_3$)$_2$C(—CH$_2$O—)$_2$ | 2,2-bis(methyleneoxy)propane |
| CH$_3$—C(—CH$_2$O—)$_3$ | 1,1,1-tris(methyleneoxy)ethane |
| CH$_3$CH$_2$C(CH$_2$O—)$_3$ | 1,1,1-tris(methyleneoxy)propane |
| C(CH$_2$O—)$_4$ | Tetra(methyleneoxy)methane |
| —C$_6$H$_4$— | 1,3-phenylene, 1,4-phenylene |

-continued

| | |
|---|---|
| —O— | oxy |
| —S$_r$— | thio, dithio (r = 1,2) |
| —SC$_6$H$_4$S— | dithiophenylene |
| O[CH$_2$C(CH$_2$O—)$_3$]$_2$ | 1,1,1,5,5,5-hexa(methyleneoxy)-3-oxapentane |

Alternatively, R$^3$ is selected from the same group as R$^4$.

R$^4$ represents a bivalent radical derived from telomers or cotelomers obtained from the same group of olefins and perfluoroalkyl vinyl ethers as R$^1$.

Preferred embodiments of R$^4$ include but are not limited to the telechelic telomers and cotelomers
—C$_l$H$_{2l}$—C$_3$F$_6$  (C$_2$ClF$_3$)$_n$(T)C$_3$F$_6$—C$_l$H$_{2l}$—,
—C$_l$H$_{2l}$—C$_2$F$_4$(C$_2$ClF$_3$)$_u$  (T)(C$_2$F$_4$)$_t$(C$_2$F$_3$ORf)$_q$—C$_2$F$_4$C$_l$H$_{2l}$—,  —C$_l$H$_{2l}$C$_3$F$_6$(C$_2$ClF$_3$)$_u$
(T)(C$_2$F$_4$)$_t$(C$_3$F$_6$)$_q$—C$_3$F$_6$—C$_l$H$_{2l}$—,  —C$_l$H$_{2l}$—C$_3$F$_6$(C$_2$ClF$_3$)$_p$(T)(C$_3$F$_6$)$_q$—C$_3$F$_6$C$_l$H$_{2l}$—,  —C$_l$H$_{2l}$—(C$_2$H$_2$F$_2$)$_p$(T)(C$_3$F$_6$)$_q$—C$_l$H$_{2l}$—,
—C$_l$H$_{2l}$(C$_2$F$_4$)$_p$(T)(C$_2$F$_3$OR$_f$)$_q$—C$_l$H$_{2l}$—,
—C$_l$H$_{2l}$(C$_2$H$_2$F$_2$)$_t$(C$_2$F$_4$)$_u$(T)(C$_3$F$_6$)$_q$  —C$_l$H$_{2l}$— and
—C$_3$H$_6$O(CF$_3$)$_2$C—C$_6$H$_4$—C(CF$_3$)$_2$OC$_3$H$_6$—.

The values for l, m, n, p, q, t and u are as defined for R1;

T is selected from —C$_2$F$_4$—, —C$_3$F$_6$—, —C$_2$ClF$_3$—, [C$_6$F$_x$H$_{(4-x)}$]— and O[C$_6$F$_x$H$_{(4-x)}$]$_2$—, where x is from 2 to 4, inclusive; and the repeating units of said cotelomers are randomly distributed along the chain.

R$^5$ represents a telechelic oligomer derived from a compound selected from the group consisting of aromatic carbonates, aromatic ether-ketones, aromatic ether sulfones, aromatic imides, aromatic ether-imides, aromatic amides, aliphatic amides, cycloaliphatic amides, aromatic ethers and aromatic thioethers, aromatic esters, aliphatic esters, heterocyclic aromatic amidourethanes, aliphatic urethanes and aromatic urethanes, Representative repeating units that can be present in R$^5$ include but are not limited to:

| | |
|---|---|
| —COOC$_6$H$_4$OC$_6$H$_4$O— | an aromatic carbonate block |
| —COOC$_6$H$_4$C(CA$_3$)$_2$C$_6$H$_4$O— | an aromatic carbonate block where A represents hydrogen or fluorine |
| —C$_6$H$_4$COC$_6$H$_4$O— | an aromatic ether-ketone block |
| —C$_6$H$_4$COC$_6$H$_4$OC$_6$H$_4$O— | an aromatic ether-ketone block |
| —C$_6$H$_4$COC$_6$H$_4$OC$_6$H$_4$C(CA$_3$)$_2$—C$_6$H$_4$O— | an aromatic ether-ketone block |
| —C$_6$H$_4$SO$_2$C$_6$H$_4$OC$_6$H$_4$OC$_6$H$_4$O— | an aromatic ether-sulfone block |
| —C$_6$H$_4$SO$_2$C$_6$H$_4$OC$_6$H$_4$C(CA$_3$)$_2$C$_6$H$_4$O— | an aromatic ether-sulfone block |
| —N(CO)$_2$C$_6$H$_2$(CO)$_2$NC$_6$H$_4$— | an aromatic imide block |
| —N(CO)$_2$C$_6$H$_3$OC$_6$H$_4$C(CA$_3$)$_2$C$_6$H$_4$OC$_6$H$_3$(CO)$_2$NC$_6$H$_4$N— | an aromatic ether-imide block |
| —NHC$_6$H$_4$NHCOC$_6$H$_4$CO— | an aromatic amide block |
| —NHC$_6$H$_{12}$NHCOC$_4$H$_8$CO— | an aliphatic amide block |
| —NHC$_6$H$_{12}$NHCOC$_6$H$_{10}$CO— | a cycloaliphatic amide block |
| —OC$_6$H$_4$— | an aromatic ether unit |
| —SC$_6$H$_4$— | an aromatic thioether unit |
| —COC$_6$H$_4$—COOC$_l$H$_{2l}$O— | an aromatic-aliphatic ester unit |
| —NC$_4$H$_8$NCONHC$_6$H$_4$CO— | a heterocyclic aromatic amido urethane unit |
| —CONHC$_6$H$_3$(CH$_3$)NHCOOC$_4$H$_8$O— | an aliphatic-aromatic urethane unit |

The products of this invention are synthesized starting from selected telomers and cotelomers of certain fluoroolefins, the precursors of R$^1$ and R$^4$ in the preceding formulae. These (co)telomers are then linked using known chemical reactions to organic groups or polymers containing hydrogenated aliphatic or aromatic hydrocarbon radicals and hetero atoms such as oxygen, sulfur, and nitrogen.

The final products can be prepared either directly from the fluoroolefin (co)telomers or from intermediate products prepared by reacting the (co)telomers with organic compounds, including polymers, containing at least one group that will react with the (co)telomer and at least one additional group such as carboxyl, hydroxyl, mercapto, amino, isocyanato, reactive halogens such as chlorine and bromine. These intermediate products are then reacted with aliphatic or aromatic organic compounds, including polymers, containing at least one group that will react with the intermediate product. The organic compound is optionally fluorinated.

The classes int which the present products fall include but are not limited to esters, ethers, sulfides, disulfides, sulfones, imides, amides, urethanes and combinations thereof. Polymeric forms of the present products include but are not limited to polyesters, polyethers, polyetheresters, polyetherketones, polyether sulfones, polyetherimides, polysulfides, and polyurethanes.

The fluorinated portion of the present compounds impart thermal and chemical resistance, resistance to thermally induced oxidation in air, low surface energy that results in high wetability and lubricity, low dielectric constant, high dielectric strength and low refractive index.

The organic compounds that are reacted with the fluorinated telomer are selected to achieve the best balance of thermochemical resistance and physical properties.

As a non-limitative example, if the final product is designed to be used as a lubricant or hydraulic fluid, the fluorinated part contributes low friction and high wetability properties.

In addition to providing a stable chemical bond, the organic compounds used to prepare the final products and the aforementioned intermediates should contribute to the compatibility and solubility in addition to the anti-wear and anticorrosion properties imparted by the product. This combination of properties is not easily achieved by presently available polyfluorinated lubricants, which are relatively insoluble.

As an example, if the final product is designed to be used as a thermoplastic polymer, the fluorinated part contributes anti-adhesion, good theology, hydrolipophobicity, optical transmission and electrical insulation. The organic co-reactant will be selected to contribute to mechanical resistance, cohesion and, if necessary, feasibility of crosslinking reactions. The combination of the two components allows multifunctional use of the final products, such as an anti-wear insulating materials, optical guide, anti-wear conductive ink or anti-wear hydrophobic coupling agent for inorganic or polymeric fibers and other complex and high performing compounds.

THE FLUOROOLEFINS AND TELOMERS THEREOF

The radicals represented by $R^1$ and $R^4$ in the general formula for the present compounds are prepared from fluorinated telomers and cotelomers that are, in turn, prepared from fiuoroolefins containing two or three carbon atoms. In some instances a perfluoroalkyl vinyl ether can be used as a co-monomer. The fluoroolefins can contain at most one chlorine or two hydrogen atoms per molecule, with the proviso that chlorine and hydrogen are not present in the same molecule. The remaining substituents on the carbon atoms of the fluoroolefins are fluorine atoms.

If a very high thermal stability is desired for the final compound when chlorotrifluoroethylene is used to synthesize the respective telomers or cotelomers with non-hydrogenated vinyl compounds, care must be taken during the formation of the telomer of cotelomer and the endcapping step to avoid the presence of a chlorine atom on each of two adjacent carbon atoms that form the sequence =CCl—CCl= or the sequence =HC—CCl=. This precaution will avoid dehalogenation or dehydrohalogenation at high temperatures in the presence of metals and/or oxygen and/or catalysts, which decreases the stability of the final compounds or polymers during use.

The perfluoroalkyl group present on the perfluoroalkylvinyl ethers that can be cotelomerized with chlorotrifluoroethylene or tetrafluoroethylene in accordance with the present invention can be perfluorinated methyl, ethyl or propyl radical.

The fluorinated olefins and vinyl ethers, referred to hereinafter as fluorovinyl compounds, used to prepare the present telomers and cotelomers are selected from the classes described in detail in a subsequent portion of this specification and are polymerized in the proper sequence if the final compound is to exhibit the high levels of chemical inertness and other properties required for critical conditions of use at high temperature, and aggressive environments.

A preferred method for preparing the telomers or cotelomers is by a radical initiated telomerization of one or more fluorinated vinyl compounds. These fluorovinyl compounds are chlorotrifluoroethylene, referred to hereinafter as CTFE, vinylidene fluoride (VDF), hexafluoropropene (HFP), 1H-pentafluoropropene, 2H-pentafluoropropene, tetrafluoroethylene (TFE), trifluoroethylene, perfluoromethyl vinyl ether, perfluoroethyl vinyl ether, and perfluoropropyl vinyl ether. Of these compounds, chlorotrifluoroethylene, vinylidene fluoride and trifluoroethylene can be telomerized individually.

Binary and ternary mixtures of vinyl compounds that can be cotelomerized are listed in the definition of $R^1$, and include
(1) chlorotrifluoroethylene and a fluoropropene selected from the group consisting of hexafluoropropene and 2-hydropentafluoropropene,
(2) chlorotrifluoroethylene and hexafluoropropene,
(3) chlorotrifluoroethylene and tetrafluoroethylene,
(4) chlorotrifluoroethylene, tetrafluoroethylene and fluoropropene selected form the group consisting of hexafluoropropene and 2-hydropentafluoropropene,
(5) vinylidene fluoride and a fluoropropene selected from the group consisting of hexafluoropropene, 1-hydropentafluoroprene and 2-hydropentafluoropropene
(6) tetrafluoroethylene and a perfluoroalkyl vinyl ether,
(7) tetrafluoroethylene, chlorotrifluoroethylene and perfluoroalkyl vinyl ether,
(8) tetrafluoroethylene and a perfluoroalkyl vinyl ether, and
(9) tetrafluoroethylene, vinylidene fluoride and a fluoropropene selected from the group consisting of hexafluoropropene, 1-hydropentafluoropropene and 2-hydropentafluoropropene,
where the alkyl radicals of said perfluoroalkyl vinyl ethers contain from 1 to 3 carbon atoms.

The telomerization and cotelomerization of the fluorovinyl compounds can be initiated by bromo- or iodosubstituted telogens represented by the formula $R_fZ$ or ZTZ, where Rf and T are as previously defined in this specification and Z is bromine or iodine. These telogens belong to a group that includes but is not limited to $CF_3I$, $C_2F_5I$, n— or iso— $C_3F_7I$, n—$C_4F_9I$, $CF_3CFBrCF_2Br$, $CF_2Br$ $CFClBr$, $CF_2ICF_2I$, $I(C_2F_4)_nI$ (n=2– 10); $C_2F_3ClBrI$ and $C_3F_6BrI$ derived from addition of BrI to the fluoroolefins $C_2F_3Cl$ and $C_3F_6$; $C_6F_xH_{4-x}I_2$ (diiodofluoro benzene), and $O(C_6FxH_{4-x}I)_2$ diphenyl ether), where x is from 2 to 4, $CF_3CFCII$.

The telomers and cotelomers prepared from the foregoing monoiodo or monobromo telogens are linked through the radicals $R^2$ to the other components of the present compounds and polymers using methods described in the following paragraphs to prepare the compounds and polymers represented by the preceding formulae I, II and III.

The telomerization process of the fluorinated vinyl compounds initiated by said telogens can be promoted by heating or through activation by gamma-rays, ultra-violet irradiation, organic peroxide initiators, redox systems containing copper or iron or other salts and amines or other reducing agents, metal carbonyls derived from elements in groups VI, VII and VIII of the periodic table of the elements, alkylated boron compounds with the addition of stoichiometric amounts of oxygen.

Preferred catalysts for these reactions include benzoyl peroxide, di-t-butyl peroxide, t-butylperoxypivalate and metal carbonyls where the metal is manganese, iron or chromium. The reaction can be conducted in the presence of organic solvents including but not limited to 1,1,2-trichlorotrifluoroethane, t-butyl alcohol and mixtures thereof. Catalysts such as persulfate red-ox systems can also be included when the telomerization is carried out in aqueous dispersion.

The temperature of telomerization ranges from ambient to 140° C. if the process is activated by irradiation or by catalyst, or in the range of 140° to 220° C. if the process is thermally activated.

The pressure under which the reaction is conducted can range from ambient up to about 60 atmospheres, and care should be taken to exclude oxygen from the telomerization reaction.

When the telomer or cotelomer of non-hydrogenated vinyl compounds contains units derived from $C_2ClF_3$, and the highest thermal stability is desired, to avoid possible dehalogenation or dehydrohalogenation, the telomerization process and the endcapping process must be conducted in order to minimize or forbid the sequences =ClC—CCl= and =ClC—CH=.

In any instance, telomers or cotelomers of chlorotrifluoroethylene with other non-hydrogenated vinyl compounds, having one or two reactive terminal groups such as —CFClBr or —CFClI, must be reacted in a final step, following removal of unreacted chlorotrifluoroethylene from the reaction vessel with a perfluoolefin such as $C_3F_6$ or $C_2F_4$ in a process referred to herein as pre-end capping. The final products are then end capped with a hydrogenated radical that can be made by reaction with ethylene or with other reagents such as unsaturated compounds like acrylic acid, 3-butenoic acid or by coupling with other bromo or iodo organic compounds.

REACTIONS OF THE DERIVATIVES OF THE FLUORINATED TELOMERS AND OLIGOMERS TO FORM THE COMPOUNDS OF FORMULAE I, II, AND III

The compounds represented by formula I can be obtained using well known reactions starting from derivatives of the fluorinated telomers and oligomers represented by the radicals $R^1$ and $R^4$.

In summary, the preferred reactions for preparing the fluorinated compounds represented by formula I from fluorotelomers or cotelomers according to the present invention include but are not limited to:

1) $R_fX+M'+M''\rightarrow R_f(M')_p(M'')_qX$ (A) M', M''= fluoroolefins and/or perfluoroalkyl vinyl ethers 2) If $M'=C_2ClF_3$, $A+RCF=CF_2\rightarrow R_f(M')_p(M'')_q CF_2—CFRX$ (B) R=F or $CF_3$ (a pre-end-capping reaction)

3) $B+C_2H_4\rightarrow R_f(M')_p(M'')_qCF_2—CFRC_2H_4X$ (C) (an end-capping reaction)

The same reaction (3) can be carried out on the intermediate (A) to obtain $C^1$:

4) B + $CH_2$=CH—COOH 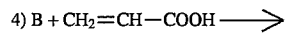

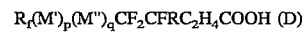

This reaction is described in U.S. Pat. No. 3,651,105 (1972), the relevant portions of which are incorporated by reference.

Reaction 4 can be carried using intermediate A to obtain $D^1$

5) $C^1+KCN\rightarrow R_f(M')_p(M'')_qC_2H_4CN$ (E) Reaction disclosed in French Pat. No. 1,599,703 (1970)

6) $E+LiAlH_4\rightarrow R_f(M')_p(M'')_qC_3H_6NH_2$ (F)

Reaction disclosed in U.S. Pat. No. 3,810,874 (1974), the relevant portions of which are incorporated by reference.

7) E $\xrightarrow{H_2SO_4}$ $R_f(M')_p(M'')_qC_2H_4COOH$ (G)

8) $Cl^1$ or C $\xrightarrow{SC(NH_2)_2}$ $\xrightarrow{NH_4OH}$

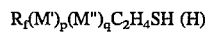

Reaction disclosed in Ger. Offen. No. 2,013,103 (1971)

10) $C_1$ (or C) + $H_2SO_4\longrightarrow R_f(M')_p(M'')_qC_2H_4OH$ (L)

11) R*COF $\xrightarrow{KF}$ $\xrightarrow{BrCH_2CH=CH_2}$

R*$CF_2OCH_2$—CH=$CH_2$ + KBr (Q)

R*COF = P or P'

12) R*COF or $NaBH_4^-\xrightarrow{H_2}$

R*$CH_2OH$ $\xrightarrow{BrCH_2CH=CH_2}$

R*$CH_2OCH_2$—CH=$CH_2$ ($Q^1$)

13) R*$CF_2OH$(or R*$CH_2ONa$) $\xrightarrow{Br(CH_2)_nCOOCH_3}$ $\xrightarrow{H_2O}$ R*$CA_2O(CH_2)_nCOOH$ (R)

(A = F, H; n = 1,2), see Tetraedron Lett. 28, p. 2424 (1974).

14) $R_fCH_2OH \xrightarrow[\text{Pyridine}]{\text{Tosyl chloride}}$ R $CH_2OTos$ (S)

Reaction 14 disclosed in J. Am. Chem. Soc., 55, p. 345, (1933)

15) $R_fCOOCH_3 \xrightarrow{NaBH_4}$ $R_fCH_2OH$ (T)

The foregoing compounds C, L, S, T are used according to the invention as reactive intermediates to obtain products containing ether groups using some variation of the Williamson reaction.

The compounds of type D, G and R are used as intermediates to obtain products containing a carboxylic ester group.

When a fluorinated carboxylic acid is used as a reactant, the carboxyl group is separated by at least two carbon atoms from a fluorinated carbon atom. Acids of this type have a dissociation constant $K_a$ in aqueous solution lower than $7\times10^{-5}$. This assures a good hydrolytic stability of the respective ester. The alcohol portion of the ester is a primary alcohol where the carbinol group is linked to a ternary carbon. The resultant ester is more stable to thermally induced hydrolysis and to heating due to the absence of the β-hydrogen on carbon adjacent to the methanol group (6-ring back biting effect. This effect is discussed in "Synthetic Lubricants", R. Gunderson, page 197, Reinhold Press Corp.).

A related class of the present compounds are stable esters derived from polyvalent alcohols including but not limited to 2,2-dimethyl-1, 3-propandiol, 1,1,1-tris(hydroxymethyl)ethane, 1,1,1-tris (hydroxymethyl)propane, pentaerythritol and dipentaerythritol The carboxyl group of the acid is at least two carbon atoms removed from a fluorinated carbon atom. Aromatic carboxylic acids such as the isomeric phthalic acids are used when a polymeric compound is the objective of the reaction.

One class of preferred esters is obtained starting from one of these polyhydroxylated alcohol and said fluorinated monocarboxylic acid derived from fluorinated telomers and/or oligomers of type $R^1$. When the molecular structure of the ester has been controlled with regard to the average molecular weight and the molecular disorder (obtained either by random sequences of the different co-monomeric units along the telomeric chains or by random esterification of the polyalcohol by different acid residues, or by using a mixture of telomeric and oligomeric acids series), the esters are liquids at room temperature and are useful as high performance lubricants, hydraulic fluids, ingredients for greases, and electrically insulating fluids for electronics.

One particularly useful class of esters corresponding to general formula II has the structure:

$$R^{20}[CH_2OCOC_1H_{21}(CFR^6CF_2)_i(M')_p(M'')_qR_f]_j, \quad \text{IIA}$$

where j is from 2 to 6; l is from 2 to 4, and the value of the numerals represented by the other letters are as disclosed in the preceding sections of this specification. The structure of the radical represented by $R^{20}$ is dependent upon the value of j. Possible structures include but are not limited to:

| $R^{20}$ | j |
|---|---|
| $(CH_3)_2C=$ | 2 |
| $CH_3C\equiv$ or $C_2H_5C\equiv$ | 3 |
| $=C=$ | 4 |
| $\equiv C—C\equiv$ | 6 |

One other series of products that, according to the invention can be structured to have the discrete molecular weight necessarily for existing as a stable fluid at a temperature of 200° C.–250° C. and that is also represented by the formula II (where j=2, $R^3$ is derived from bifunctional cotelomers or oligomers of the type $R^4$, and $R^1$ is a group derived from monofunctional cotelomers or oligomers), has a structure of type IIB and is derived from 2,2-dimethylpropandiol:

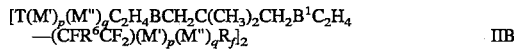

$$[T(M')_p(M'')_qC_2H_4BCH_2C(CH_3)_2CH_2B^1C_2H_4 \\ —(CFR^6CF_2)(M')_p(M'')_qR_f]_2 \quad \text{IIB}$$

In this formula $R_f$ and T are as defined in the preceding specification, B and $B^1$ can be different or the same group and are —C(O)O— (oxycarbonyl) or —O(oxy) and the indexes p, q have different values for the different units M', M".

The compounds described in the preceding specification having a ratio of monovalent R1 radicals to bivalent $R^4$ radicals of 2 also can be represented by the formula III.

Another series of products represented by the formula II is formed by sulfides and is type IIC:

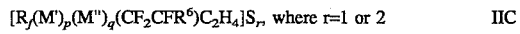

$$[R_f(M')_p(M'')_q(CF_2CFR^6)C_2H_4]S_r, \text{ where r=1 or 2} \quad \text{IIC}$$

General formula III of the present compounds represents high molecular weight polymeric compounds that enter the dominion of elastomers, thermoplastics and resins. Along the chain represented by formula III random or block sequences can be combined and linked through ether, carboxylic, esters, urethanes, dicarboxyimido bond types, and others, and the resulting polymeric structures are polyesters, polyetheresters, polyether-urethanes, polyether-imides, poly(ether ketones) and others.

Examples of polymers represented by formula IIIA include but are not limited to:

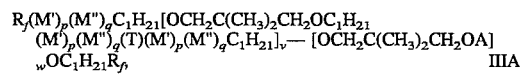

$$R_f(M')_p(M'')_qC_1H_{21}[OCH_2C(CH_3)_2CH_2OC_1H_{21} \\ (M')_p(M'')_q(T)(M')_p(M'')_qC_1H_{21}]_v— [OCH_2C(CH_3)_2CH_2OA] \\ _wOC_1H_{21}R_f, \quad \text{IIIA}$$

where A can be selected from group comprising:

| | |
|---|---|
| —COC₆H₄CO— | block w is a polyester |
| —CONHC₆H₃(CH₃)NHCO— | block w is a polyurethane |
| —CONHC₆H₁₂NHCO— | block w is a polyurethane |
| —C₆H₄COC₆H₄— | block w is a polyether ketone |
| —C₆H₄SO₂C₆H₄— | block w is a polyether sulfone |
| —C₆H₃(CO)₂NC₆H₄N(CO)₂C₆H₃— | block w is a polyetherimide |

The preferred procedures for preparing the various condensation type polymers include but are not limited to those described in the following sections.

FOR THE ETHER BONDS:

(a) A Williamson reaction between dibromo or diiodo alkylene $R_f(C_2H_4X)_2$ or activated aromatic chloro or fluoro derivatives and sodium or potassium alcoholates preferably in an aprotic solvent such as acetonitrile, acetone, tetrahydrofuran, dimethylsulfoxide and hexamethylphosphoramide. The reaction is preferably conducted in the presence of 18-crown-6 ether to increase the nucleophilic character of the oxy-ion. This procedure can be used also for preparing the thioethers from the corresponding mercaptan.

(b) Coupling of dibromo derivatives or diiodo derivatives promoted by copper or zinc in one step or two steps with other reagents containing active sites (active hydrogen, organometallic, other halogen-substituted functional groups) to form an intermediate organic compound, in the presence of aprotic solvent type dimethylsulfoxide, tetrahydrofuran, hexamethylphosphoramide, and others.

FOR THE CARBOXYLIC ESTER BONDS (c) Condensation of bis-methyloltosylate or of dibromo or diiodo derivatives and sodium or potassium salt of dicarboxylic acids (in some cases also formed in situ by $K_2CO_3$ and free dicarboxylic acids) in the presence of a solvent selected from Acetone (dry or 95%), THF, with the optional presence of 18-crown-6 ether.

(d) Transesterification of methyl ester and excess of polyalcohol activated by compounds of titanium, zinc or antimony as known to the skilled of the art.

FOR THE AROMATIC BLOCKS

When non-commercially available, the aromatic blocks are preferentially prepared separately, using for example, $ClC_6H_3(CO)_2NC_6H_4N(CO)_2C_6H_3Cl$, and this block ending in the active halogens is reacted with the dipotassium methylol block as described before.

The properties of said polymers depend on the range of molecular weight, on the rigidity or flexibility of the combined blocks, that can be balanced using as components different fluorotelomer blocks, fluorooligomer blocks, aromatic blocks, polyether or polyester or polycarboximide blocks.

The content of fluorine and the presence or absence of polar bonding groups that are involved with aromatic blocks do effect physical and chemical properties. Moreover a dosed percentage of unit carrying groups able to be used for crosslinking the polymers can act to improve the mechanical and thermal resistance of the polymers. As unsaturated compounds can be used terminal vinyl or allyl ether of fluorotelomers or oligomers such as that obtained according to the foregoing equations 14 and 15 or other unsaturated compounds such as 5-norbornene-endo-2,3-dicarboxylic derivatives or endo-bicyclo (2.2.2)-oct-5-ene-2,3-dicarboxylic acid derivatives, or 4-cyclohexene-1,2-dicarboxylic acid derivatives or maleic or itaconic acid derivatives; the cross-linking reaction is provided by peroxides such as bis(t-butyl-i-propylbenzene) peroxide at 150° C. or by reaction of selected unsaturated groups with polyhydrosilanes catalyzed by platinum compounds.

The properties of the final products or polymers according to the invention and depending on their structure include, but are not limited to:

For polyethers and polyesters represented by formula II:
low dielectric constants, particularly for compounds formed by cotelomers containing units of chlorotrifluoroethlene, hexafluoropropene, tetrafluoroethylene and trifluoroethylene
good optical properties and low refractive index
high solvent resistance
good resistance to aggressive chemicals
good viscosity index (viscostaticity) for compounds having half of the substituents formed by oligomers of fluorooxirane or fluorooxetane.

For elastomeric products with structures of polyester and polyether esters not containing aromatic rings and represented by formula III:
good flexibility at low temperature
good thermomechanical resistance
good rheological properties For thermoplastic elastomer and resins containing aromatic and poly ring structure and rigid telomeric blocks and represented by formula III:
good rheological properties in melt
good mechanical resistance (especially for the post reticulated items)
good electrical properties The aforementioned properties allow the use of the liquids and wax compounds as lubricants, hydraulic fluids, ingredients for greases that can be added with anti-wear, anticorrosion, antioxidant additives to increase the life of metal parts that are under rotating or reciprocating lubricated contact; particularly as anti-wear additives can be used the polyfluoroalkyl disulfides obtained according to the invention; the use of selected liquids as electrical insulating for electronics; the use of the elastomer products as sealants or as high consistency rubbers that can be reinforced with silica or special carbon black fillers to obtain items resistant to oils and solvents also at temperatures up to 250° C.; the use of plastics and resins as materials that are to be used for protective thin layers and as film for electronics, molecular layers over fibers, both inorganic and organic, to impart anti-friction properties and resistance to water that is beneficial for the long life of composite materials.

Without further elaboration it is believed that one skilled in the art, using the preceding description, can utilize the present invention to its fullest extent.

The following Examples describe preferred embodiments of this invention and should not be interpreted as limiting the invention as defined in the accompanying claims. Unless otherwise specified all parts and percentages in the Examples are by weight and viscosities are based on a temperature of 25° C.

EXAMPLE 1

NEOPENTYL GLYCOL ESTER DERIVED FROM A COTELOMERIC FLUOROALKANECARBOXYLIC ACID

A 1000 cc—capacity stainless steel autoclave was charged with 600 parts of $C_4F_9I$, 110 parts vinylidene fluoride, 14 parts of ferric chloride and 5 parts of nickel. The autoclave was then sealed and the contents heated at a temperature of 175° C. for 48 hours. At the end of this time period the gas in the autoclave was vented and the liquid in the reactor was poured into a 5% aqueous hydrochloric acid solution. The organic layer was washed with water and dried. The $^{19}F$ nuclear magnetic resonance (NMR) spectrum of this liquid (A), obtained in 75% yield, exhibited a maximum at −38.85 ppm, characteristic of the —$CF_2I$ group, using trichlorofluoromethane as the internal standard. This is consistent with the structure $C_4F_9CH_2CF_2I$.

25 parts of liquid (A) and 55 parts of hexafluoropropene were reacted in a 200 cc-capacity autoclave for 62 hours at a temperature of 210° C. The results of analyses of the resultant liquid (B) by gas liquid chromatography using a SE column and by $^{19}F$ NMR were consistent with the structure $C_4F_9CH_2CF_2(C_3F_6)_mI$, where the value for B was 1 in 70 percent of the molecules and was 2 in the remaining 30 percent.

An autoclave was charged with 22 parts of liquid B, 40 parts of t-butyl alcohol, 0.05 parts of cuprous chloride and 1.5 parts of ethanolamine. The autoclave was then sealed and ethylene was added in an amount sufficient to achieve a pressure of 30 atmospheres. The contents of the autoclave were heated at a temperature of 140° C. for 16 hours. The results of analysis of the liquid (C) in the autoclave by gas-liquid chromatography and infra-red spectroscopy were consistent with the structure $C_4F_9CH_2CF_2(C_3F_6)_mC_2H_4I$. The $^{19}F$ NMR spectrum, using trichlorofluoromethane as the internal standard, exhibited maxima at −178-9 ppm, characteristic of =CF—, and in the region of 074.3, characteristic of —$CF_3$.

A glass reactor was charged with 16.9 parts of liquid (C), 16 parts of dimethyl sulfoxide and 4.2 parts of potassium cyanide. The resultant mixture was stirred while being maintained at a temperature of from 60° to 900° C. for 4 hours. The contents of the reactor were then poured into water, extracted with diethyl ether and the ether solution was, in turn, dried over anhydrous sodium sulfate. Removal of the ether yielded a liquid (D) that exhibited the infra-red absorption maximum at 2240 cm$^{-1}$ characteristic of the nitrile group and was consistent with the structure $C_4F_9CH_2CF_2(C_3F_6)_mC_2H_4CN$.

An eight part portion of lipaid (D) was hydrolyzed by reacting it with 5.5 parts of a 95% aqueous sulfuric acid solution in the presence of 1.6 parts of acetic acid and 2.3 parts of water for 4 hours at a temperature of 100° C. The reaction product was poured into water, extracted with ether, and the ether solution was washed with water. The infra-red spectrum of the liquid (E) remaining following removal of the ether exhibited the absorption maxima in the range from 1680 to 1720 cm$^{-1}$ characteristic of the carboxyl group.

Five parts of liquid (E) were reacted with 15 parts of $SOCl_2$ for five hours at the boiling point of the mixture. The infrared spectrum of the liquid (F) remaining following removal of the unreacted $SOCl_2$ exhibited an absorption maximum in the range from 1700 to 1750 cm$^{-1}$ characteristic of the COCl group.

A glass reactor was charged with 4 parts of neopentyl glycol, 42 parts of liquid (F), 50 parts of carbon tetrachloride, 50 parts of Freon(R) 113, a liquid chlorofluorocarbon, and 20 parts of pyridine.

The contents of the reactor were stirred for 3 hours under ambient conditions. At the conclusion of this period the reaction mixture was filtered, washed with an aqueous solution of sodium bicarbonate, and the solvent removed from the organic layer by evaporation. The infra-red spectrum of the wax-like residue exhibited an absorption peak centered at 1720 cm$^{-1}$, characteristic of the carboxylic ester group, and was consistent with the structure $$C(CH_3)_2[CH_2OCOC_2H_4(C_3F_6)_mCF_2CH_2C_4F_9]_2$$

EXAMPLE 2

PREPARATION OF A POLY(FLUOROALKYLENE TEREPHTHALATE)

A 200 cc-capacity stainless steel autoclave was charged with 25 parts of the telogen 1,2-iodotetrafluoroethane, 9 parts of vinylidene fluoride and 22 parts of hexafluoropropene. The autoclave was then sealed the contents were heated at a temperature of 210° C. for 3 days. At this time the reactor was allowed to cool and the gaseous reagents were vented. Analysis of the liquid (A) in the reactor by gas-liquid chromatography using an SE column indicated the absence of the initial telogen.

Distillation of liquid (A) yielded four fractions. One of these fractions (4.5 parts) boiled from 65° to 100° C. under a pressure of 30 torr. The $^{19}$F NMR spectrum of this liquid exhibited maxima at −38, −62 and −106 ppm using CFCl$_3$ as the internal standard, and was consistent with the structure IC$_2$F$_4$CH$_2$CF$_2$I.

3.5 parts of a second fraction was collected over the range from 100°–125° C. under a pressure of 30 torr. The $^{19}$F NMR spectrum of this fraction (B) exhibited maxima in the range from −183 to −185 ppm, characteristic of internal units derived from hexafluoropropene, and was consistent with the telomer I(C$_2$F$_4$)(C$_3$F$_6$)$_n$(CH$_2$CF$_2$)$_m$I, where the values of m and n were 1.

The residual liquid (C) consisted essentially of a mixture of telomers exhibiting the general formula of fraction (B), where the sum of the values of m and n were 2, 3 and 4.

Fractions (B) and (C) were combined in a 200 cc-capacity autoclave together with 0.005 parts of cuprous chloride and 1.5 parts of ethanolamine. The autoclave was then sealed and sufficient ethylene was added to achieve a pressure of 30 atmospheres. The contents of the autoclave were heated at a temperature of 140° C. for 16 hours. At the completion of this reaction the gaseous materials were vented and the liquid (D) in the reactor was washed sequentially with 5% aqueous hydrochloric acid solution and water, after which it was dried. The proton NMR spectrum exhibited maxima in the range from 2.7 to 3.5 ppm using tetramethylsilane as the internal standard, and was consistent with a mixture of telomers of the structure $$IC_2H_4(C_2F_4)(CH_2CF_2)_m(C_3F_6)_nC_2H_4I \qquad (D)$$

where the sum of m and n was 2, 3 and 4

Five parts of liquid (D) were dissolved in 20 parts of a mixture (E) containing a 5:3:0.5 volume ratio of acetonitrile:dimethyl sulfoxide:methanol. The resultant solution was added to a glass reactor containing 1.9 parts of terephthalic acid, 0.3 part of 18-crown-6 ether and 50 parts of solvent mixture E.

The resultant mixture was heated for 16 hours at a temperature of from 60° to 80° C. An aliquot equivalent to 1/10 of the reaction mixture was removed from the reactor and poured into a large volume of hot water. The water-insoluble layer was washed once with water, dried, extracted with benzene twice and dried again. The infra-red absorption spectrum of the final liquid exhibited an intense absorption in the region from 1700 to 1730 cm$^{-1}$ characteristic of the ester group and a weak peak at 1570 cm$^{-1}$ characteristic of the unreacted carboxyl group. The intensity ratio of the peaks centered at 1700 and 1570 cm$^{-1}$ was 4:1, respectively.

Another one part of liquid (D) dissolved in solvent mixture (E) was added to the reactor and the resultant mixture was heated for an additional 4 hours at a temperature of 60°–80° C. The contents of the reactor was then poured into hot water and the solid material that precipitated was washed with water, followed by a washing with benzene.

The final solid material (F) was insoluble in Freon(R) 113 and diethyl ether, but was soluble in N,N-dimethyl-formamide, from which it could be precipitated by the addition of water.

A sample of the solid material was pressed into a drawable film by placing it on an electrically heated plate. The infra-red spectrum of the solid exhibited an increase in the ratio of intensity exhibited by the peaks at 1700 and 1570 cm$^{-1}$, indicating that an increase in molecular weight of the polymer could be achieved using this procedure of step-wise chain extension.

The polymer did not exhibit signs of decomposition at temperatures in the range from 300° to about 340° C. There was evidence of decomposition in the presence of air as the temperature approached 350° C. The I.R spectrum and thermal properties of the polymer were consistent with a polyester derived from terephthalic acid. The polymer was therefore assigned the structure $$-[COC_6H_4COO(C_2H_4)C_2F_4\ (C_3F_6)_n(CH_2CF_2)_mC_2H_4O]_x-.$$

That which is claimed is:

1. Fluorinated compounds represented by the formula $$R^1[(R^2R^4)_v(R^2R^5)_w]_kR^2R^1$$

wherein $R^1$ is selected from the group consisting of
  (a) monovalent telomers of a fluorinated olefin selected from the group consisting of chlorotrifluoroethylene, vinylidene fluoride and trifluoroethylene, and
  (b) monovalent cotelomers of combinations selected from the group consisting of
    (1) chlorotrifluoroethylene and a fluoropropene selected from the group consisting of hexafluoropropene and 2-hydropentafluoropropene,
    (2) chlorotrifluoroethylene and hexafluoropropene,
    (3) chlorotrifluoroethylene and vinylidene fluoride,
    (4) chlorotrifluoroethylene and tetrafluoroethylene,
    (5) chlorotrifluoroethylene, tetrafluoroethylene and a fluoropropene selected form the group consisting of hexafluoropropene and 2-hydropentafluoropropene,
    (6) vinylidene fluoride and a fluoropropene selected from the group consisting of hexafluoropropene, 1-hydropentafluoropene and 2-hydropentafluoropropene,
    (7) vinylidene fluoride, chlorotrifluoroethylene and hexafluoropropene,
    (8) tetrafluoroethylene, vinylidene fluoride and chlorotrifluoroethylene, and
    (9) tetrafluoroethylene, vinylidene fluoride and a fluoropropene selected from the group consisting of hexafluoropropene, 1-hydropentafluoropropene and 2-hydropentafluoropropene, $R^2$ represents a bivalent radical connecting $R^5$ with $R^1$ and $R^4$, and is selected from the group consisting of dimethylene, trimethylene, ethyleneoxy, trimethyleneoxy, bistrifluoromethyl)methyleneoxy, hexafluoroisopropylidene, and 2,2-dimethyl-1,3-trimethylene; $R^4$ is a bivalent radical derived from telomers and cotelomers of the same olefins as $R^1$; and $R^5$ represents the divalent group —OC(O)A(O)CO—, where A is alkylene or arylene and said group is derived from an aromatic or aliphatic diester; k is from 1 to 500, inclusive; v is from 1 to 100, inclusive; and w is from 1 to 10, inclusive.

2. A compound according to claim 1 wherein the telomers and cotelomers represented by $R^1$ are selected from the group represented by the formulae

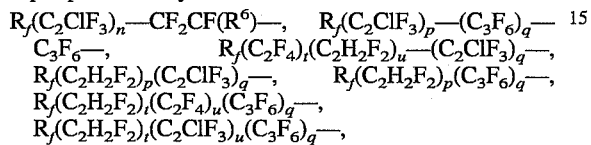

where $R_f$ is —$CF_3$, —$C_2F_5$, —$C_3F_7$, or —$C_4F_9$; the telomers and cotelomers represented by $R^4$ are selected from the group represented by the formulae

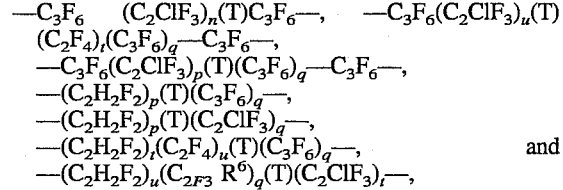

where T is selected from —$C_2F_4$—, —$C_3F_6$—, —$C_2ClF_3$—, [$C_6F_xH_{(4-x)}$]— and O[$C_6F_xH_{(4-x)}$]$_2$—, x is from 2 to 4, inclusive; $R^6$ represents fluorine or a trifluoromethyl group; the value of n is from 1 to 10 inclusive; the value of p/q is from 2 to 10, inclusive and the value of p+q is from 2 to 10; the value of t+u/q is from 2 to 10, inclusive, the value of t/u is from 0.1 to 10, and the value of t+u+q is from 2 to 20, inclusive; and the repeating units of said cotelomers are randomly distributed along the chain.

* * * * *